(12) United States Patent
Peitz et al.

(10) Patent No.: US 10,370,311 B2
(45) Date of Patent: Aug. 6, 2019

(54) HYDROGEN-ASSISTED ADSORPTION OF SULPHUR COMPOUNDS FROM OLEFIN MIXTURES

(71) Applicant: Evonik Degussa GmbH, Essen (DE)

(72) Inventors: Stephan Peitz, Oer-Erkenschwick (DE); Guido Stochniol, Haltern am See (DE); Dietrich Maschmeyer, Recklinghausen (DE); Helene Reeker, Dortmund (DE); Reiner Bukohl, Marl (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/165,882

(22) Filed: May 26, 2016

(65) Prior Publication Data

US 2016/0347690 A1 Dec. 1, 2016

(30) Foreign Application Priority Data

May 28, 2015 (EP) .................................. 15169655

(51) Int. Cl.

| | |
|---|---|
| *C07C 7/12* | (2006.01) |
| *C07C 7/00* | (2006.01) |
| *B01D 15/00* | (2006.01) |
| *B01J 20/06* | (2006.01) |
| *B01J 20/08* | (2006.01) |
| *C10G 25/00* | (2006.01) |
| *C07C 2/06* | (2006.01) |
| *C07C 2/56* | (2006.01) |
| *C07C 5/327* | (2006.01) |
| *C07C 7/04* | (2006.01) |
| *C07C 7/10* | (2006.01) |
| *C07C 7/163* | (2006.01) |
| *C07C 7/167* | (2006.01) |
| *C07C 41/09* | (2006.01) |
| *C07D 307/60* | (2006.01) |
| *C10G 45/04* | (2006.01) |
| *C10G 45/22* | (2006.01) |
| *C07C 2/58* | (2006.01) |
| *C07C 5/48* | (2006.01) |

(52) U.S. Cl.
CPC ................ *C07C 7/12* (2013.01); *B01D 15/00* (2013.01); *B01J 20/06* (2013.01); *B01J 20/08* (2013.01); *C07C 2/06* (2013.01); *C07C 2/56* (2013.01); *C07C 2/58* (2013.01); *C07C 5/327* (2013.01); *C07C 5/48* (2013.01); *C07C 7/04* (2013.01); *C07C 7/10* (2013.01); *C07C 7/163* (2013.01); *C07C 7/167* (2013.01); *C07C 41/09* (2013.01); *C07D 307/60* (2013.01); *C10G 25/003* (2013.01); *C10G 45/04* (2013.01); *C10G 45/22* (2013.01); *B01J 2220/42* (2013.01)

(58) Field of Classification Search
CPC ........... C07C 7/12; C07C 7/167; C07C 7/163; C07C 7/10
See application file for complete search history.

(56) References Cited

U.S. PATENT DOCUMENTS

| | | | |
|---|---|---|---|
| 4,391,677 A | * | 7/1983 | Harris .................... C07C 7/005 203/28 |
| 4,983,367 A | | 1/1991 | Denny et al. |
| 4,996,181 A | * | 2/1991 | Denny .................. B01D 53/02 502/174 |
| 6,042,798 A | | 3/2000 | Masuda et al. |
| 8,859,834 B2 | | 10/2014 | Boeing |
| 8,889,935 B2 | | 11/2014 | Maschmeyer |
| 9,200,216 B2 | | 12/2015 | Boeing |
| 9,260,386 B2 | | 2/2016 | Peitz et al. |
| 2006/0191821 A1 | | 8/2006 | Nicolaos et al. |
| 2007/0003455 A1 | | 1/2007 | Morita et al. |
| 2007/0135665 A1 | | 1/2007 | Wiese et al. |

(Continued)

FOREIGN PATENT DOCUMENTS

| | | |
|---|---|---|
| CA | 2110223 | 5/1994 |
| DE | 1568864 A1 | 7/1970 |

(Continued)

OTHER PUBLICATIONS

Melpolder et al. (Composition of naphtha from fluid catalytic cracking, Industrial and Engineering Chemistry, vol. 44, No. 5, pp. 1142-1146) (Year: 1952).*
Torres et al. (Improving the modeling of hydrogen solubility in heavy oil cuts using an Augmented Grayson Streed (ASG) approach, Oil and gas Science and Technology—Rev. IFP Energies nouvelles, vol. 68 (2013), No. 2, pp. 217-233, (Year: 2013).*
Wiese, F. Nierlich, DGMK-Tagungsbericht [German Society for Petroleum and Coal Science and Technology, Conference Report] Mar. 2004, ISBN 3-936418-23-3.

(Continued)

*Primary Examiner* — Youngsul Jeong
(74) *Attorney, Agent, or Firm* — Michael Best & Friedrich LLP

(57) ABSTRACT

The invention relates to a process for purifying hydrocarbon mixtures, in which a contaminated hydrocarbon mixture comprising olefins having three to eight carbon atoms is at least partly freed of sulphur-containing contaminants by contacting it with a solid sorbent, the hydrocarbon mixture being exclusively in the liquid state during the contact with the sorbent. The problem that it addressed was that of virtually completely removing sulphur compounds present in the mixture without forming new sulphur compounds again at the same time. At the same time, 1-butene present therein was not to be lost in the purification of the mixture. Finally, the sorbent used was to have a high sorption capacity, be very substantially free of carcinogenic constituents and be readily available. This problem is solved by using a sorbent based on copper oxide, zinc oxide and aluminium oxide in a particular composition, and by conducting the purification in the presence of a small amount of hydrogen.

11 Claims, No Drawings

(56) References Cited

U.S. PATENT DOCUMENTS

| | | | |
|---|---|---|---|
| 2007/0034552 A1 | 2/2007 | Turbeville et al. | |
| 2008/0306316 A1 | 12/2008 | Becker et al. | |
| 2009/0071876 A1* | 3/2009 | Masuda ............... | B01J 20/0225 |
| | | | 208/226 |
| 2014/0161701 A1 | 6/2014 | Macleod et al. | |
| 2016/0152527 A1 | 6/2016 | Peitz et al. | |
| 2016/0326442 A1 | 11/2016 | Geilen et al. | |

FOREIGN PATENT DOCUMENTS

| | | |
|---|---|---|
| DE | 2846614 A1 | 4/1980 |
| DE | 3914817 A1 | 11/1990 |
| DE | 10160486 A1 | 6/2003 |
| DE | 102004018753 A1 | 11/2005 |
| DE | 102005062354 | 6/2007 |
| DE | 102008007081 A1 | 8/2009 |
| DE | 102013225724 A1 | 6/2015 |
| EP | 0064464 A1 | 11/1982 |
| EP | 0320979 A2 | 6/1989 |
| EP | 0125689 B2 | 10/1989 |
| EP | 0354316 B1 | 2/1990 |
| EP | 0398251 | 11/1990 |
| EP | 0600406 | 6/1994 |
| EP | 0395857 B1 | 8/1994 |
| EP | 1029839 A1 | 8/2000 |
| EP | 1192981 | 4/2002 |
| EP | 1686166 | 8/2006 |
| JP | S5569521 | 5/1980 |
| JP | 2013094732 | 5/2013 |
| NO | 2005044959 | 5/2005 |
| WO | 199428089 A1 | 12/1994 |
| WO | 2014009148 A1 | 1/2014 |
| WO | 2014009159 A2 | 1/2014 |

OTHER PUBLICATIONS

Friedlander et al., "Make plastic olefins via n-butane dimerization," Hydrocarbon Process., Int. Ed. (1986) 65 (2. Sect.1), pp. 31 to 33.
G. A. Dziabis, "UOP Merox Process" in Robert Meyers, Handbook of Petroleum Refining Processes, 3rd Edition, 2004 McGraw-Hill.
W. Turbeville et al., "The chemistry of coper-containing sulfer adsorbents in the presence of mercaptans," Cat. Today, 519-525 (2006).
R. H. Höppener, E. B. M. Doesburg, J. J. F. Scholten: Preparation and characterization of stable copper/zinc oxide/alumina catalysts for methanol synthesis. Appl. Catal. 25 (1986) 109-119.
European Search Report for Application No. 16170613.0 dated Sep. 29, 2016 (9 pages).
Gulf Cooperation Council Patent Office Examination Report for Application No. 2016-31392 dated Feb. 10, 2019, 3 pages.

* cited by examiner

HYDROGEN-ASSISTED ADSORPTION OF SULPHUR COMPOUNDS FROM OLEFIN MIXTURES

CROSS-REFERENCE TO RELATED APPLICATION

This patent application claims the benefit of priority to European Application No. 15169655.6, filed on May 28, 2015, the disclosure of which is incorporated by reference herein in its entirety, and priority to which is hereby claimed.

The invention relates to a process for purifying hydrocarbon mixtures, in which a contaminated hydrocarbon mixture comprising olefins having three to eight carbon atoms is at least partly freed of sulphur-containing contaminants by contacting it with a solid sorbent based on copper oxide, zinc oxide and aluminium oxide, the hydrocarbon mixture being exclusively in the liquid state during the contact with the sorbent.

Hydrocarbons are compounds consisting exclusively of carbon and hydrogen. The nomenclature of the hydrocarbons is based on the number of carbon atoms present per molecule of the hydrocarbon. In abbreviated notation, the prefix $C_n$ is commonly used, where n is said number.

$C_4$ hydrocarbons are consequently compounds consisting exclusively of carbon and hydrogen, where the number of carbon atoms per molecule is four. Important representatives of the $C_4$ hydrocarbons are the alkenes and alkanes having four carbon atoms, namely the butenes and butanes.

Alkenes (synonym: olefins) are hydrocarbons which have one C=C double bond in the molecule. Alkanes (paraffins), on the other hand, are hydrocarbons which have only single bonds. They are therefore also referred to as saturated. Alkanes and alkenes having the same number of carbon atoms usually occur together in raw material mixtures in the chemical industry. Since alkenes are more reactive because of their unsaturated double bond, they are suitable as a starting material for chemical reactions. Alkanes, which are far less reactive, can generally be used only as fuel. Because of their higher reactivity, olefins are more valuable than paraffins. The greater the proportion of alkenes in a raw material mixture compared to the alkanes, the more costly the raw material.

Mixtures of $C_4$ hydrocarbons are raw materials from downstream petrochemistry. They originate, for example, from steamcrackers (so-called "crack C4"), from catalytic crackers (so-called "FCC C4" (FCC: "fluid catalytic cracking") or "DCC C4" (DCC: "deep catalytic cracking"), from pyrolysis ("pyrolysis C4"), from MTO or MTP processes (MTO: "methanol to olefins", MTP: methanol to propylene) or dehydrogenations of isobutane and n-butane. The most common are $C_4$ hydrocarbons from steamcrackers (crack C4) and from catalytic crackers (FCC C4). Mixtures of $C_4$ mixtures of different origin are also traded, called "$C_4$ cut". For the purpose of utilizing the individual components, the $C_4$ mixtures have to be divided into their constituents with maximum purity.

The workup of $C_4$ streams from steamcrackers or catalytic crackers is described in principle in K.-D. Wiese, F. Nierlich, DGMK-Tagungsbericht [German Society for Petroleum and Coal Science and Technology, Conference Report] 2004-3, ISBN 3-936418-23-3. A comprehensive overall process description can be found in DE102008007081A1.

The aspects of $C_4$ workup that are relevant to this invention are outlined briefly hereinafter.

Technical $C_4$ hydrocarbon mixtures from the above-described sources typically contain not only saturated and monounsaturated compounds but also polyunsaturated compounds. Before individual compounds can be isolated from these mixtures, it is frequently necessary to remove other compounds to the maximum possible degree. This can be effected by physical methods, for example distillation, extractive distillation or extraction, but also by a selective chemical conversion of the components to be removed. Particular attention has to be paid to the maximum possible removal of the contaminants such as oxygen-, nitrogen- and sulphur-containing components present in the $C_4$ hydrocarbon mixture, since these can have adverse effects on the individual process steps as catalyst poisons. While these impurities are typically present only in traces in crack C4, they may also be present in higher concentrations, for example, in FCC C4 streams.

$C_4$ hydrocarbon mixtures from steamcrackers or fluidized catalytic crackers typically have the main components listed in Table 0 (contaminants not shown).

TABLE 0

Typical compositions of crack C4 and FCC C4

| Component | Crack C4 [% by wt.] | FCC C4 [% by wt.] |
| --- | --- | --- |
| isobutane | 1-3 | 15-45 |
| n-butane | 6-11 | 5-15 |
| 1-butene | 14-20 | 5-20 |
| 2-butenes | 4-8 | 20-35 |
| isobutene | 20-28 | 10-20 |
| 1,3-butadiene | 40-45 | less than 1 |

The composition of the raw materials may vary significantly according to the origin of the material. The $C_4$ components listed are supplemented by hydrocarbons having fewer or more carbon atoms, and contaminants such as mercaptans, sulphides, disulphides, nitrogen- and oxygen-containing compounds in small amounts.

In one variant, the workup of FCC $C_4$ can be effected in such a way that the concentration of isobutane is first lowered by means of a distillative step in a distillation to a value of less than 5% by weight. At the same time, the low boilers present in the mixture (for example $C_3$ hydrocarbons, light oxygen-, nitrogen- and sulphur-containing compounds) are removed or minimized. In the subsequent step, in a column, all the high boilers (for example $C_5$ hydrocarbons, heavy oxygen-, nitrogen- and sulphur-containing compounds) are removed via the bottom. In the next step, isobutene is removed, for example by reacting it with methanol to give methyl tert-butyl ether (MTBE), and the latter is removed by distillation. If pure isobutene is to be obtained, the methyl tert-butyl ether can subsequently be cleaved again to isobutene and methanol.

For further workup of the $C_4$ mixture, the polyunsaturated compounds still remaining have to be converted with the aid of a selective hydrogenation process to the corresponding monounsaturated and saturated compounds. Now 1-butene and remaining isobutane can be removed by distillation in sufficient purity, and the remaining 2-butenes and the n-butane can be subjected to further workup.

Frequently, the 2-butenes are converted by oligomerization, more specifically by dimerization to octenes. This forms one molecule having eight carbon atoms from two molecules each having four carbon atoms. The octenes can subsequently be converted by means of hydroformylation to PVC plasticizer alcohols. The saturated C4 hydrocarbons that remain after the olefins have been depleted can especially be used as propellants for aerosols.

An oligomerization is understood to mean a process in which higher alkenes having 6-20 carbon atoms are formed from olefins, such as, more particularly, from propene and butenes. An example of a process employed industrially is the nickel-catalysed OCTOL process, which is described in detail in Hydrocarbon Process., Int. Ed. (1986) 65 (2. Sect. 1), pages 31 to 33, and in DE3914817, EP1029839 and DE102004018753. According to the OCTOL process, the oligomerization is effected in the liquid phase, and for that reason a high process intensity is achieved.

The input streams used for the individual process steps have generally already attained a high degree of purity through preceding processes in which impurities were removed again and again. However, remaining impurities can reversibly or even irreversibly deactivate the catalysts. This deactivation should of course be reduced to a minimum for economic reasons. Therefore, as many catalyst poisons as possible should be kept away from the catalyst by further purification stages.

The various catalyst poisons present in the technical $C_4$ mixtures have poisoning effects in different ways. For instance, the acidic catalyst systems or system components such as cocatalysts are poisoned almost exclusively by components which are themselves basic or at least release bases as a result of further reactions. A particularly typical example of such substances is acetonitrile which, as a very weak base, is comparatively difficult to remove by sorption processes. However, it reversibly poisons strong Lewis acids. In the presence of traces of water, it is hydrolysed via acetamide to the strong base ammonia, which then irreversibly deactivates Brønsted acids as well through formation of ammonium ions. Incidentally, even water itself is always a partial catalyst poison, but the effect thereof is generally reversible, provided that it does not contribute to the formation of stronger catalyst poisons through further reactions. For the nickel-catalysed oligomerization of butenes over the OCTOL catalyst, even a water content of about 5 ppm leads to measurable deactivation. However, the water is added onto olefins by many systems, and the alcohols formed are oxidized by the standard catalyst systems via a transfer hydrogenation, with hydrogenation of other unsaturated components, until thermodynamic equilibrium has been attained.

The metal complex catalysts too are sensitive to basic substances. The poisoning effect is usually manifested primarily via the deactivation of the acidic cocatalyst.

The metal component of the catalysts, in contrast, is attacked particularly strongly by components such as sulphur in the form of particular compounds, and this under particular circumstances irreversibly destroys the metal hydride or metal complex through formation of sparingly soluble sulphides. Since the metals are generally in very low oxidation states, sulphur compounds that are able to oxidize the metals to a relatively high oxidation state, for example di- and polysulphides, are particularly effective. Different sulphur compounds are thus able to have quite different primary effects. While, for example, disulphides react extremely efficiently to give thioethers and sulphur, which then oxidizes the metal hydrides to form sulphides, the primary effect of thioethers themselves at first is probably solely as a Lewis base. Through further processes and reactions, which are generally not even known in detail, with further trace components in the system, however, they also lead ultimately—albeit much more slowly—to the formation of metal sulphides as well.

According to the above statements, for economically successful operation of a plant for fractionation of hydrocarbon mixtures into their constituents of value with the aid of catalytic reaction units, the problem is thus to protect the catalysts used with maximum efficacy from catalyst poisons and especially from sulphur compounds. The more reactant the catalyst is to specifically convert, the more strongly this applies, and so this applies particularly to heterogeneous catalysts, for example those of the OCTOL process.

In industrial practice, alkaline scrubs remove sulphur-containing poisons from propene and butene streams. In these scrubs, hydrogen sulphide and mercaptans react particularly efficiently. In general, the alkaline scrubbing solutions are regenerated by oxidation with air.

Such a scrubbing effort is offered for industrial use by UOP LLC under the MEROX® name. (G. A. Dziabis, "UOP MEROX PROCESS" in Robert Meyers, Handbook of Petroleum Refining Processes, 3rd Edition, 2004 McGraw-Hill).

In the MEROX® process, the mercaptans are oxidized in the aqueous scrubbing solution to di- and polysulphides, which are removed as oily phase. However, a small portion of these di- and polysulphides remains dissolved or suspended in the aqueous alkali metal hydroxide solution, and it is often not possible even by scrubbing this aqueous phase with a scrubbing oil or the like to quantitatively remove this residue before recycling into the scrubbing, such that the mercaptans are substantially removed but, on the other hand, small amounts of di- and polysulphides are introduced back into the stream. As just mentioned, these are sulphur components which convert the metal hydrides that are essential to the reaction to sparingly soluble metal sulphides and hence irreversibly deactivate the catalyst. Typically, for example, the streams of FCC C4 contain about 100 to 200 ppm of sulphur. After the MEROX® scrub, this content has then typically been reduced to a value below 10 ppm, and the sulphur compounds then consist predominantly of the di- and polysulphides mentioned, but also of higher mercaptans.

In practice, a portion of the poisons, through skilful arrangement of separating operations, for example distillations, can also be directed into fractions in which they no longer come into contact with sensitive catalysts. Frequently, however, this is not possible to the extent that seems desirable with regard to the purity of the streams, such that sorbents have to be inserted upstream of the catalysts, in order to assure the required purity.

Sorbents are solid substances that are capable of binding another substance, called the sorbate, if they come into contact with the sorbate. The binding is effected at the surface of the sorbent through physical and/or chemical effects. In this respect, a distinction is made between physical and chemical adsorption. Since the mode of action of a sorbent is not always unambiguously clear, reference is made here to a sorbent, without attributing the effect.

From a technical point of view, sorbents should generally be distinguished into those which are regeneratable and those that irreversibly convert or chemically bind the catalyst poisons.

Regeneratable sorbents used are frequently molecular sieves and zeolites. Regeneratable sorbents bind soiling materials only with moderate strength. In the course of regeneration of the sorbent, conditions such as higher temperatures and lower pressures, for example, under which the sorbent releases the sorbate again, are established. This property leads to a relatively low capacity before breakthrough. In addition, high operating costs often arise through discharge and flushing of the sorbent and through the provision and disposal of the regenerating gases or else of the liquid streams.

Irreversible sorbents, in contrast, are not regenerated but disposed of after breakthrough. They therefore have to be available and disposable inexpensively. Since irreversible sorbents chemically bind the adsorbate, the permeability thereof with respect to the substances to be adsorbed is lower than in the case of regeneratable sorbents. Irreversible sorbents therefore achieve better purity levels than regeneratable sorbents.

EP 0 064 464 A1 describes catalyst materials usable particularly for desulphurization of hydrocarbon batches. The catalyst materials contain copper oxide and are based on a support composed of alumina or type X or Y zeolite. A matter of concern is the obligatory content of cadmium oxide, since cadmium is classified as carcinogenic. Carcinogenic substances can be handled and disposed of only with high cost and inconvenience, and so particularly the irreversible use of such catalyst materials is uneconomic.

EP 0 354 316 B1 describes the cadmium-free fine desulphurization of liquid $C_4$ hydrocarbon mixtures over zeolites containing copper, silver and zinc. The preferred temperature range is between 50 and 130° C., the preferred pressure 1 to 50 bar. The weight hourly space velocity is reported as 1 to 40 $h^{-1}$. Even though the sorbent described here does not contain any potentially hazardous cadmium, this material is likewise uneconomic because of its high silver content of at least 2% by weight.

Nickel-containing oligomerization catalysts are particularly prone to catalyst poisons. Hydrocarbon mixtures having two to four carbon atoms often serve as substrate for oligomerizations such as the OCTOL process. In order to effectively remove catalyst poisons, it has been found to be useful to pass such streams over a molecular sieve before entry into the oligomerization. For instance, EP0395857B1 describes a process in which a desulphurization of refinery propene, prior to oligomerization thereof, is effected over a copper-exchanged X zeolite at a temperature of 120° C., a pressure of 50 bar abs. and a weight hourly space velocity of 0.75 $h^{-1}$. Under these conditions, propene is supercritical.

Since these simple molecular sieves are readily available and do not present any potential hazard to health, they are nowadays the sorbents of choice in industrial practice for fine desulphurization of $C_3$ to $C_8$ hydrocarbon mixtures. Since unmodified molecular sieves bind the contaminants essentially by physical means, sorbents of this kind can be regenerated. However, the sorption capacity thereof is lower compared to chemical sorbents, such that only moderate purities are achievable by fine desulphurization over unmodified zeolites. In order to compensate for this drawback, zeolites are modified in such a way that they also chemically arrest impurities; however, this in turn restricts the regeneratability of the modified zeolites.

WO2014/009159A1 discloses the use of pyrophoric nickel for irreversible sulphur adsorption upstream of oligomerization plants. In one experiment, this sorbent is used successfully to remove dimethyl sulphide from a $C_4$ olefin mixture. A disadvantage of this sorbent is its pyrophoric properties, which make it difficult to handle. Industrial use is therefore possible only with restrictions.

German patent application 102013225724.4, which was still unpublished at the filing date, describes the purification of liquid olefin mixtures by means of a copper/zinc/aluminium catalyst which is normally used in methanol synthesis. The purification takes place in the absence of hydrogen. Experiments demonstrate that this material virtually completely binds all the sulphur compounds that typically occur in C4 olefin mixtures (especially mercaptans). It has the advantage over the pyrophoric nickel material of being easier to handle.

A disadvantage of this $CuO/ZnO/Al_2O_3$ sorbent is that it releases a portion of the sulphur introduced again in the form of disulphides, more specifically dimethyl disulphide, diethyl disulphide, ethyl methyl disulphide and similar substances. Disulphide formation takes place in the sorbent itself; in this respect, the material appears to be catalytically active: two thiolate units are apparently joined oxidatively to form disulphides on the CuO surface. This admittedly occurs only to a minor degree.

A significant disadvantage of the $CuO/ZnO/Al_2O_3$ sorbents described in DE102013225724 is the low adsorption capacity for sulphur or sulphur compounds of only about 1.4% by weight. By comparison, WO2014/009159A1 promises a sulphur capacity of about 25%.

WO94/28089 discloses the use of elemental Cu-containing adsorbents for irreversible sulphur adsorption. These are obtained from CuO-containing precursors by prior reduction of the CuO with hydrogen to give elemental Cu. It is stated therein that elemental Cu is much more reactive compared to mercaptans and elemental sulphur than CuO. Disulphides are obviously not retained efficiently by means of such materials. A further disadvantage is the need to reduce the CuO in the hydrogen stream to elemental Cu at high temperatures prior to the use thereof in an adsorption reactor. This either requires a costly heat-resistant reactor or ex situ conditioning with subsequent installation of the adsorbent under a protective atmosphere.

EP0320979A2 also describes desulphurizing agents based on copper oxide, zinc oxide and aluminium oxide. However, the oxidic sorbent is reduced with hydrogen prior to use, and so it is ultimately used in metallic form.

US2007034552 discloses the use of $CuO/ZnO/Al_2O_3$ as materials that scavenge sulphur compounds. It was shown on the basis of butanethiol as sulphur component in naphtha as hydrocarbon mixture, in the case of adsorption in the liquid phase, that between 3.7% and 10% by weight of sulphur (calculated in elemental form) can be retained on the various $CuO/ZnO/Al_2O_3$ materials. However, the juncture of breakthrough through the adsorption bed was defined as being when 80% of the sulphur input is detected in the adsorber output. This means that the adsorbent effect at this juncture has in fact already been lost. For downstream processes that are sensitive even to a few thousand ppb of sulphur, such a definition of breakthrough is completely unsuitable.

W. Turbeville et al., Cat. Today, 519-525 (2006) describes materials that are analogous to US2007034552 and their adsorption kinetics. It is clear from the graphs relating to sulphur breakthrough that acceptable definitions of breakthrough, for example breakthrough at 20% of the feed sulphur content, occur at much lower run times. For instance, the period until attainment of the 20% breakthrough mark in all the experiments described is about a quarter of the 80% mark. This means that, in the application case of a 20% breakthrough limit which is of great industrial relevance, the service life is shortened to a quarter, and so the exchange of the adsorber has to be undertaken four times more frequently. A further disadvantage of the materials and experiments described by Turbeville et al. is the permanent passage of disulphides formed from mercaptans, which do not appear to be significantly adsorbed.

Against this background, the problem addressed by the invention was that of specifying a process for purifying liquid olefin mixtures, in which sulphur compounds present in the mixture are virtually fully removed without forming new sulphur compounds again to a significant degree at the same time. After purification, a sulphur content of well below 1 ppm is to be assured, such that downstream catalytic processes such as oligomerizations in particular are not poisoned. A further important problem addressed by this invention is that of specifying a process that leads to a distinct increase in capacity or service life of the sorbent used. Moreover, in the purification of the mixture, products of value present therein, for example 1-butene, are not to be lost, since the process is also to be suitable for purifying those hydrocarbon mixtures having a high proportion of valuable 1-butene, which would be isomerized to less valuable 2-butenes in the case of an unsuitable sorption material. Finally, the sorbent used is to be very substantially free of carcinogenic constituents and be readily available.

These problems are solved by using a sorbent having the following composition that adds up to 100% by weight:
  copper oxide: 10% by weight to 60% by weight (calculated as CuO);
  zinc oxide: 10% by weight to 60% by weight (calculated as ZnO);
  aluminium oxide: 10% by weight to 30% by weight (calculated as $Al_2O_3$);
  other substances: 0% by weight to 5% by weight;
and by conducting the purification in the presence of hydrogen.

This is because it has been found that such a $CuO/ZnO/Al_2O_3$ system releases virtually no sulphur compounds of any kind when small amounts of hydrogen are present during contact with the contaminated hydrocarbon mixture. The outstanding ability of the material to bind sulphur compounds, for example mercaptans, is actually enhanced by the presence of a hydrogen. The capacity of the sorbent is therefore increased. Furthermore, sulphur components which, according to the current state of knowledge, are barely retained on corresponding adsorbents are also bound to an enhanced degree. Since the hydrogen is added only in small amounts, reactive products of value such as 1-butene are very substantially conserved, since they are barely lost as a result of unwanted hydrogenation. Unwanted side reactions of the by-products are barely promoted by the sorption material used.

The present invention therefore provides a process for purifying hydrocarbon mixtures, in which a contaminated hydrocarbon mixture comprising olefins having three to eight carbon atoms is at least partly freed of sulphur-containing contaminants by contacting it with a solid sorbent in the presence of hydrogen, the hydrocarbon mixture being exclusively in the liquid state during the contact with the sorbent, and wherein the sorbent has the following composition that adds up to 100% by weight:
  copper oxide: 10% by weight to 60% by weight (calculated as CuO);
  zinc oxide: 10% by weight to 60% by weight (calculated as ZnO);
  aluminium oxide: 10% by weight to 30% by weight (calculated as $Al_2O_3$);
  other substances: 0% by weight to 5% by weight.

A practical advantage of the process of the invention is that said $CuO/ZnO/Al_2O_3$ system need not be specially prepared but is easily commercially available, namely as the catalyst as normally used in methanol synthesis.

Methanol is an important commodity chemical which is synthesized from a gas mixture of hydrogen, carbon monoxide and carbon dioxide in the presence of solid copper/zinc/aluminium catalysts. Since methanol is produced globally in very large volumes, the copper/zinc/aluminium catalysts required for the purpose are readily available. An essential aspect of the invention is to utilize such methanol catalysts as sorbents for desulphurization of olefin mixtures in the presence of hydrogen.

Solid copper/zinc/aluminium catalysts for methanol synthesis have been described many times in the patent literature:

For instance, DE2846614C3 discloses a process for preparing methanol from a gas mixture of CO, $CO_2$ and $H_2$ at temperatures of 200 to 350° C. in the presence of a catalyst containing 38.3% Cu, 48.8% Zn and 12.9% Al.

DE1568864C3 points out that synthesis gas should be desulphurized for methanol production, since copper catalysts can easily be poisoned with sulphur. The copper/zinc/aluminium catalyst described here contains more than 35% by weight of copper; the zinc content is 15% to 50% by weight. The aluminium content is reported as 4% to 20% by weight.

EP0125689B2 describes a catalyst for methanol synthesis, which comprises copper oxide and zinc oxide as catalytically active substances, and also—as a thermally stabilizing substance—aluminium oxide. In the unreduced state, catalyst precursors produced by way of example have, for instance, 65% to 68% by weight of CuO, 21% to 23% by weight of ZnO and 10% to 12% by weight of $Al_2O_3$. The specific surface area is 100 to 130 $g/m^2$. The methanol synthesis is effected at 250° C. and 50 bar.

Similar methanol catalysts having 63% to 65% by weight of CuO, 24% to 27% by weight of ZnO and 10% to 11% by weight of $Al_2O_3$ are described in DE10160486A1.

A catalyst having a comparatively low copper content and high zinc content (43.2% by weight of CuO, 47.0% by weight of ZnO and 10.2% by weight of $Al_2O_3$) was produced in U.S. Pat. No. 4,279,781. However, the catalytic activity thereof in methanol synthesis was rated as comparatively poor.

The preparation of copper oxide, zinc oxide, aluminium oxide catalysts for methanol synthesis has been addressed scientifically by R. H. Höppener, E. B. M. Doesburg, J. J. F. Scholten: Preparation and characterization of stable copper/zinc oxide/alumina catalysts for methanol synthesis. Appl. Catal. 25 (1986) 109-119.

Because of the great industrial significance of the synthesis of methanol, a commodity chemical, copper/zinc/aluminium catalysts have not just been described in theoretical terms in the scientific literature and in patent literature but are also readily commercially available. Examples include MegaMax® 700 and 800 from Clariant (formerly Süd-Chemie) and Haldor Topsoe's Mk-101 and Mk-121.

The disposal of this material is comparatively unproblematic, since no substances classified as carcinogenic are present. Incidentally, the recycling of such sorbents is economically attractive, since this material contains a large amount of valuable copper.

The suitability of a methanol catalyst for desulphurization of $C_3$ to $C_8$ hydrocarbon mixtures is surprising because the workup of such mixtures is generally effected in the liquid phase, since the hydrocarbons having more than two carbon atoms are liquefied with a low level of expenditure and can then be processed with a high process intensity. However, methanol synthesis is effected exclusively in the gas phase. It was not to be expected that materials intended for gas phase catalysis would also be suitable for liquid phase sorption.

In principle, any commercially available Cu/Zn/Al catalyst having said composition is suitable as a solid sorbent for purification of the $C_3$ to $C_8$ hydrocarbon mixtures in the presence of hydrogen. However, preference is given to using those catalysts which have the following composition:
- copper oxide: 30% to 45% by weight (calculated as CuO);
- zinc oxide: 30% to 50% by weight (calculated as ZnO);
- aluminium oxide: 10% to 15% by weight (calculated as $Al_2O_3$);
- further metal oxides: 0% to 2% by weight;
- graphite: 0% to 3% by weight;
- other substances: 0% to 1% by weight.

Useful further metal oxides in this context are, for example, iron oxides or magnesium oxides. Heavy metal oxides, which are known to be hazardous to health, for example cadmium or lead or chromium, should not be present if at all possible. Relatively small amounts of graphite or magnesium stearate serve as binders for better shaping of the sorbent. "Other substances" in this context are understood to mean production-related contaminants of the sorbent.

With regard to the shaping, the sorbent may be present in powder form or in the form of granules. In addition, the sorbent can be pressed into a defined form, for example into spheres, pellets, tablets, rings, tori or trilobular shaped bodies.

The use of material having a high copper oxide surface area is advantageous because the reaction rate of the adsorption and of the conversion correlates therewith, and these materials also have a higher sorption capacity. Preferably, the first sorbent has a copper oxide surface area of at least 50 $m^2/g$, preferably 100 $m^2/g$, based on the copper oxide content thereof. This promotes the sorptive action. The surface area is determined by nitrogen sorption.

Suitable methods for the production of the sorbent are in principle all the technical methods that lead to a solid having sufficient stability for handling. It encompasses essentially the two steps of:
i) providing a porous framework material composed of aluminium oxide;
ii) blending the framework material with copper oxide and zinc oxide.

It is possible to use copper oxide powder, copper carbonate powder or hydroxide-containing copper compounds, and mixtures thereof. In the case of copper, it is also possible to convert a copper carbonate-containing compound, with the aid of an ammoniacal solution, fully or partly to a copper tetraammine carbonate solution which serves as starting material. These substances are mixed, in accordance with the inventive mixing ratios, together with zinc oxide, zinc carbonate or zinc hydroxide and an $Al_2O_3$-containing powder. This powder serves as framework material. As $Al_2O_3$-containing powder, it is possible to use all the polymorphs of $Al_2O_3$, and also aluminium oxide hydrate or aluminium hydroxy oxides and aluminium hydroxide. As well as $Al_2O_3$, it is also possible for $SiO_2$ to be present in portions. The individual solid components can be blended and homogenized in suitable mixers, intensive mixers or kneaders. In this process, it is customary to undertake moistening with demineralized water. Adequate mixing may be followed by any suitable shaping operation. Under some circumstances, complete or partial drying and/or grinding of the mixture is necessary beforehand. For the shaping, extruders or tableting presses, for example, are suitable. Pan pelletizers may be appropriate for these purposes. In the case of tableting, a lubrication aid such as graphite is often added to the mixture. In the case of extrusion, other organic additives suitable for establishing the necessary plasticizability of the mixture are often chosen. These include, for example, cellulose-like substances, polyethers, polyethylene glycol and others, which may under some circumstances also act as pore formers when the substances are removed wholly or partly by a thermal treatment which generally follows the shaping operation. In the case of pelletization in a corresponding pan pelletizer, the buildup agglomeration is achieved by the gradual addition of a suitable amount of water. The addition of magnesium stearate helps in the consolidation of the powder to give defined shaped bodies.

The thermal treatment is conducted in one step or in sequential steps. Water components or else organic components are removed here, and the mechanical strength of the shaped body is generally increased in the process. In addition, the necessary oxide phases are formed if the precursor materials were not yet in this form.

In another mode of preparation, nitrate salts are used in aqueous solution or the oxidic compounds are fully or partly dissolved with nitric acid. Especially in the case of the aluminium oxide-type compounds, complete dissolution is often not effected; instead, the material is modified with the aid of the acid, this operation being referred to as peptization. The peptide is then mixed with the other dissolved components as described above and processed to a shaped body. The effect of heat treatment is that the respective oxides can form from the nitrates if the temperature has been suitably chosen.

Another effect of the use of nitrate-containing salt solutions may be that a precipitation reaction has to be conducted in order to arrive at a solids mixture. The pH is adjusted with sodium hydroxide or sodium carbonate solutions. Examples thereof can be found in EP0125689B2.

In addition, it is possible to convert nitrate salt solutions to an oxidic product mixture in solid form by means of spray drying. In general, there then follow a grinding operation and a shaping operation as described above. A final heat treatment, which can also be conducted directly after the spray drying or the grinding of the constituents, brings about the necessary residual nitrate breakdown and converts the components to the oxides and consolidates the shaped body.

The above-described special production of the sorbent can be dispensed with through use of a commercially available methanol catalyst.

An essential aspect of the invention is that the purification, i.e. the contact of the contaminated hydrocarbon mixture with the sorbent, is effected in the presence of hydrogen. In this respect, the invention differs from processes discussed that are conducted in the absence of hydrogen.

The presence of hydrogen is understood to mean a content by mass of molecular hydrogen ($H_2$) of more than 1 ppm based on the total mass of the contaminated hydrocarbon mixture at the time of contact. The unit of measurement ppm here always means $10^{-6}$.

More specifically, the contaminated hydrocarbon mixture, immediately prior to contact with the solid sorbent, should contain hydrogen in a concentration between 1 ppm by weight and 10 000 ppm by weight, based on the total mass of the contaminated hydrocarbon mixture. This is because a higher hydrogen content leads to unwanted hydrogenation or hydroisomerization of products of value present in the hydrocarbon mixture, such as 1-butene in particular.

What is crucial is that the hydrogen and the hydrocarbon mixture to be purified come into contact simultaneously with the sorbent. It is not enough to treat the sorbent with hydrogen prior to contact with the hydrocarbon mixture; instead, the hydrogen has to be dissolved in the hydrocarbon mixture to be purified.

A suitable hydrogen content at the time of contact has been found to be a concentration of 1 to 10 000 ppm; again based on the total mass of the contaminated hydrocarbon mixture.

The hydrogen should be dissolved substantially completely in the contaminated hydrocarbon mixture. This means that the purification is effected in the absence of gaseous hydrogen. Because the contaminated hydrocarbon mixture is liquid in accordance with the invention, there is no troublesome gas phase at all at the time of contact. This increases the process intensity.

Since the maximum hydrogen content dissolved in homogeneous liquid form depends both on the operating pressure and on the operating temperature, a practicable hydrogen content under preferred operating conditions with temperatures between 10° C. and 150° C. and pressures between 0.5 and 3.5 MPa has been found to be from 1 ppm by weight to 1000 ppm by weight. The preferred hydrogen content has been found to be a concentration of 10 ppm by weight 500 ppm by weight; a particularly preferred hydrogen content at the time of contact has been found to be a concentration of 50 ppm by weight to 300 ppm by weight.

Technical hydrocarbon streams for which purification by the present process is the intention are generally free of hydrogen; the hydrogen concentration of typical $C_3$ and $C_4$ olefin mixtures from downstream petrochemistry is below 1 ppm by weight.

This means that the inventive concentration of hydrogen has to be established by adding hydrogen to the contaminated hydrocarbon mixture directly prior to contact, since otherwise the contaminated hydrocarbon mixture on contact would contain less than 1 ppm by weight of hydrogen.

Thus, a technical measure which permits the metered addition of hydrogen to the contaminated hydrocarbon mixture is required. This may be a commercial gas/liquid mixer since the hydrogen is fed into the liquid hydrocarbon mixture in gaseous form. Because of its low concentration, the hydrogen is fully dissolved in the liquid hydrocarbon mixture, such that the contact over the sorbent is a pure liquid/solid contact, i.e. without the presence of a gas phase.

The hydrogen concentration in the contaminated hydrocarbon mixture can easily be established by a suitable delivery system, such as a hydrogen gas regulator. Since this is standard practice in the chemical industry, it is possible in this way to achieve a high degree of automation. If required, however, the hydrogen content can be determined by gas chromatography by means of a thermal conductivity detector. This is entirely possible within the concentration ranges specified.

If an overdosage of hydrogen takes place, this is generally not detrimental to the catalysts in downstream operations. Nevertheless, the abovementioned upper limits in hydrogen concentration should be complied with, since products of value present in the stream could otherwise be lost as a result of hydrogenation and/or isomerization. The removal of possibly unconverted hydrogen is preferably conducted in an already existing distillation step, for example in the tops of the 1-butene distillation.

What is important in the context of the present invention is that the sorbent, even in the presence of said concentrations of hydrogen, has essentially no catalytic activity in respect of etherification, hydrogenation, isomerization, oligomerization or further reactions of olefins. These reactions of hydrocarbons are to proceed exclusively over the catalysts intended therefor, and not over the sorbent. For that reason, the catalysts to be protected are preferably remote from the sorbent, at least in another bed or in other apparatuses.

According to the circumstances, contact times between 0.01 and 0.2 hour are typically envisaged, but if required also longer. Since operation at elevated temperature accelerates the depletion and increases the sulphur capacity, it is advantageous to arrange it downstream of the preheaters that are usually present. Observing a particular temperature of the sorbent is crucial to its purifying capacity.

Experiments show that the contact should therefore take place at temperatures between 10° C. and 150° C., preferably between 20° C. and 130° C. and most preferably between 30° C. and 120° C. The optimal contact temperature is about 80° C. to 100° C. Since commercial methanol catalysts are used at much higher temperatures, thermal stability exists within these ranges. If the catalyst to be protected is operated at a different temperature, the sorbent should be disposed in a separate vessel, i.e. outside the reactor.

What is important is that the contaminated hydrocarbon mixture is exclusively in the liquid state during contact with the sorbent. Within the specified temperature range, this is assured by a pressure between 0.5 MPa and 3.5 MPa (corresponding to 5 to 35 bar). However, the pressure is ultimately unimportant, provided that the hydrocarbons are in the liquid state. In that case, the weight hourly space velocity (WHSV) is preferably chosen between 0.5 $h^{-1}$ and 20 $h^{-1}$. This means that between 0.5 and 20 kilograms per hour of contaminated hydrocarbon mixture are run through the sorbent per kilogram of sorbent. The sorbent is poured into a vessel with a bulk density in the range from 0.7 $kg/m^3$ to 1.5 $kg/m^3$, preferably about 1.15 $kg/m^3$. The hydrocarbon mixture to be purified is conducted through the vessel containing the bed.

In order to achieve particularly effective purification and to avoid interruptions to operation resulting from exchange of the sorbents, it is advisable to use a plurality of vessels which can be connected in series in a revolving manner such that the vessel having the highest loading is always disposed at the inlet and that with the lowest loading at the outlet. In this case, without interrupting the stream to be purified, at least one vessel can be taken out and the material present therein can be rinsed and removed, followed by refilling in an analogous manner.

The process according to the invention is suitable for the purifying of hydrocarbon mixtures including olefins having three to eight carbon atoms. Hydrocarbon mixtures of industrial relevance are regarded as being, for example, propene, n-butenes, n-pentenes, hexenes, neohexene, etc., and the saturated analogues thereof. Among these, propane/propene and the butanes/butenes are absolutely the most important. It is therefore utilized with particular preference for the purification of hydrocarbon mixtures including olefins having three and/or four carbon atoms. The entire content of ethene, olefins with at least four carbon atoms and aromatic compounds within the contaminated hydrocarbon mixture should be below 500 ppm by weight, preferably below 50 ppm by weight.

The sorbent according to the invention can be used particularly advantageously for purification of typical $C_4$ olefin streams in a state of processing immediately prior to conversion of the butenes present therein.

The process is of particularly good applicability to such mixtures, since it efficiently removes sulphur-containing contaminants that act as poisons to the heterogeneous aluminium-, silicon- or nickel-containing oligomerization catalysts.

The impurities that are to be removed in accordance with the invention from the contaminated hydrocarbon mixture are preferably organic sulphur compounds that act as catalyst poison in the subsequent workup of the hydrocarbon mixture. As well as sulphur-containing contaminants, sulphur-free catalyst poisons such as bases, amines or nitriles are also removed, these substances often being below the detection limit.

Hydrogen sulphide ($H_2S$), which is often present in significant amounts in crude natural gas and mineral oil, is no longer present in the typical chemical raw material streams, since it is already removed in the refineries or natural gas processing.

The sulphur compounds of interest which have to be removed in the present context are instead organic sulphur compounds that are typically present in raw material streams from downstream petrochemistry. These are especially:
  a) thiols having the general formula R—SH
  b) disulphides having the general formula R—S—S—R'
  c) sulphides having the general formula R—S—R' and
  d) substituted or unsubstituted sulphur-containing heterocycles, such as thiophenes and/or thiolanes in particular.

In the above-specified structural formulae, R and R' may be identical or different alkyl, aryl, cycloalkyl or alkenyl radicals, where R and R' are especially methyl, ethyl, propyl, butyl, phenyl, cyclohexyl or butenyl radicals.

These sulphur-containing impurities are at least partly but generally actually completely removed with the aid of the purification according to the invention. Preferably, the sulphur-containing impurities from the above substance classes are removed to an extent of more than 90% by weight, preferably to an extent of more than 95% by weight.

The particular advantage of the sorption material used in accordance with the invention is that it chemically adsorbs the contaminants, especially by arresting thiols present as contaminant at the surface of the sorbent. The disulphide formation from thiols that occurs without metered addition of hydrogen at the adsorber surface, in a formal sense, is an oxidative coupling of two thiols with elimination of hydrogen. The metered addition of hydrogen which is used here in accordance with the invention shifts the chemical equilibrium much further to the side of the thiols, which distinctly suppresses disulphide formation. Any disulphides already present in the C4 stream are thus likewise converted to a thiol over the sorbent and then arrested. Hydrogen-assisted chemisorption, by comparison with adsorption without metered addition of hydrogen in accordance with the invention, therefore results in a particularly high level of purification, such that the hydrocarbon mixture is freed virtually completely of thiols and disulphides present.

The chemisorption of the catalyst poisons is irreversible. For this reason, the sorbent used in accordance with the invention cannot be regenerated. This means that highly contaminated hydrocarbon streams rapidly exhaust the sorbent, such that it has to be exchanged. In the interests of economically viable operation of the purifying process, the proportion by weight of the contaminants in the contaminated hydrocarbon mixture, based on the total weight thereof, should be less than 0.2% by weight. More preferably, the contaminated hydrocarbon mixture contains less than 100 ppm by weight and more preferably less than 10 ppm by weight of impurities, in each case calculated as sulphur. In the case of such a low level of contamination, the sorbent can be operated for a very long period and additionally enables virtually complete removal of the catalyst poisons. As always, the unit of measurement ppm is understood as $10^{-6}$.

The typical raw material mixtures originating from mineral oil refineries have sulphur contents well above 0.2% by weight. For this reason, it is necessary to prepurify the raw material mixture in a prepurification stage upstream of the sorptive purification. In the prepurification stage, the more highly contaminated raw material mixture is prepurified to obtain a hydrocarbon mixture having a contamination level below 0.2% by weight.

A suitable prepurification stage is especially the above-described MEROX® scrub or a thioetherification, as disclosed in WO2014009148A1.

The inventive form of purification is especially suitable for being inserted into the flow as a safety net filter beyond a MEROX® scrub.

In this context, a safety net filter is understood to mean a second purifying instance (fine desulphurization) which is arranged beyond a first purifying instance and which has the function of conclusively keeping residual amounts of the catalyst poisons that have not been captured by the first purifying instance away from downstream reaction steps or, in the case of disrupted operation in the first instance, of ruling out immediate damage to the downstream reaction steps.

Preferably, a MEROX® scrub serves as the first purifying instance, which separates out most of the catalyst poisons in relatively large amounts in advance. In that case, only the mercaptans and disulphides which are not covered by the MEROX® scrub are retained in accordance with the invention by the sorbent described here with addition of hydrogen.

In the case of disrupted operation in the pre-purification, the safety net filter takes on the full purifying function and protects the oligomerization from immediate irreversible damage. Since the safety net filter in the normal state of operation takes on only a small amount of adsorbate, it can be designed such that it has a much smaller capacity than a MEROX® scrub typically used for pre-purification. This corresponds to the speed at which it is exhausted in the event of a fault. The suitable dimensions of the safety net filter depend on how quickly the incoming mixture can be diverted.

Thioethers, being comparatively unreactive substances, are barely removed in MEROX® scrubs. In order to avoid excessively large concentrations on contact with the adsorbent, they are preferably removed in a distillation as high boilers at a suitable point in the process procedure upstream of the adsorbent.

In combination with a prepurification stage, for example a MEROX® scrub, it is possible in that case to use the sorbent described here irreversibly without hesitation. An irreversible use in this context is understood to mean that no direct regeneration, i.e. recovery of the active sorbent, is effected as soon as it is deactivated. This does not rule out recycling of the spent sorbent by recovering the metals present therein, such as the copper in particular, by metallurgical means. This is because, in such a metallurgical treatment, the original composition of the sorbent is lost, and so it is not possible to speak of a regeneration in this context.

The process according to the invention is basically suitable for desulphurization of mixtures of hydrocarbons having three to eight carbon atoms. However, it is used with particular preference for removing poisons from $C_4$ streams that are obtained as crack C4 or as FCC C4 or the corresponding raffinates thereof in the refining of mineral oil.

Thus, the contaminated hydrocarbon mixture preferably fulfils one of the following specifications A, B, C and D, each of which adds up to 100% by weight, the stated proportions by weight each being based on the total weight of the contaminated hydrocarbon mixture:

Specification A:
isobutane 15% to 45% by weight, preferably 25% to 35% by weight;
n-butane 5% to 18% by weight, preferably 8% to 10% by weight;
1-butene 5% to 20% by weight, preferably 12% to 14% by weight;
isobutene 12% to 25% by weight, preferably 15% to 20% by weight;
2-butenes 9% to 40% by weight, preferably 20% to 30% by weight;
1,3-butadiene 0% to 3% by weight, preferably 0.5% to 0.8% by weight;
water 0% to 1% by weight, preferably less than 0.1% by weight;
sulphur-containing impurities less than 0.5% by weight, preferably less than 0.2% by weight;
hydrogen less than 1 ppm by weight.

Specification B:
isobutane 0.5% to 15% by weight, preferably 1% to 7% by weight;
n-butane 0.5% to 20% by weight, preferably 4% to 7% by weight;
1-butene 9% to 25% by weight, preferably 10% to 20% by weight;
isobutene 10% to 35% by weight, preferably 20% to 30% by weight;
2-butenes 3% to 15% by weight, preferably 5% to 10% by weight;
1,3-butadiene 25% to 70% by weight, preferably 40% to 50% by weight;
water 0% to 1% by weight, preferably less than 0.5% by weight;
sulphur-containing impurities less than 0.5% by weight, preferably less than 0.2% by weight;
hydrogen less than 1 ppm by weight.

Specification C:
isobutane 0.5% to 18% by weight, preferably 1% to 7% by weight;
n-butane 0.5% to 25% by weight, preferably 4% to 13% by weight;
1-butene 9% to 40% by weight, preferably 10% to 35% by weight;
isobutene 10% to 55% by weight, preferably 20% to 50% by weight;
2-butenes 3% to 25% by weight, preferably 5% to 20% by weight;
1,3-butadiene 0% to 5% by weight, preferably less than 0.8% by weight;
water 0% to 1% by weight, preferably less than 0.5% by weight;
sulphur-containing impurities less than 0.5% by weight, preferably less than 0.2% by weight;
hydrogen less than 1 ppm by weight.

Specification D:
isobutane 0% to 20% by weight, preferably 0% to 5% by weight;
n-butane 10% to 35% by weight, preferably 25% to 30% by weight;
1-butene 0.2% to 45% by weight, preferably 3% to 30% by weight;
2-butenes 35% to 85% by weight, preferably 50% to 75% by weight;
water 0% to 1% by weight, preferably less than 0.1% by weight;
sulphur-containing impurities less than 0.5% by weight, preferably less than 0.1% by weight;
hydrogen less than 1 ppm by weight.

Specification A describes typical FCC C4, while specification B describes typical crack C4. Specification C describes a typical raffinate I from crack C4. Specification D describes a raffinate Ill from FCC or CC4. Since such technical C4 mixtures are generally free of hydrogen, the hydrogen required in accordance with the invention has to be added prior to the contact.

The process according to the invention is therefore preferably utilized for fine desulphurization of C4 mixtures of the above-specified specifications A, B, C or D, since the sorbent has hardly any catalytic activity even in the presence of hydrogen and hence does not convert the most valuable constituent, the 1-butene, to butane or 2-butene. If the purification process is conducted under the operating conditions specified here, a conversion, i.e. loss, of 1-butene of less than 5% is to be expected.

Of course, the inventive process can be used for purifying contaminated hydrocarbon mixtures comprising value 1-butene, which are, however, not compliant to above mentioned specifications A, B, C or D. Even in such cases losses of 1-butene below 5% are to be expected.

Hence, a special embodiment of the invention concerns a process in which the contaminated hydrocarbon mixture comprises 1-butene, wherein by contact with the sorbent less than 5% of 1-butene comprised in the contaminated hydrocarbon mixture is converted.

After the contaminated hydrocarbon mixture has been freed of its catalyst poisons in accordance with the invention, the customary workup of such mixtures can be effected, without any risk of poisoning the catalysts used downstream. The typical workup steps that may follow the purification described here include:
a) extraction of 1,3-butadiene present in the hydrocarbon mixture;
b) selective hydrogenation of diolefins and/or acetylenes present in the hydrocarbon mixture to olefins;
c) oligomerization of olefins present in the hydrocarbon mixture to corresponding oligomers;
d) distillative removal of 1-butene and/or isobutane present in the hydrocarbon mixture, especially with the purpose of obtaining 1-butene and/or isobutane in high purity;
e) removal of isobutene present in the hydrocarbon mixture by conversion of the isobutene with water to tert-butanol and/or with methanol to methyl tert-butyl ether;
f) dehydrogenation of butanes present in the hydrocarbon mixture to butenes;
g) oxidative dehydrogenation of butenes present in the hydrocarbon mixture to butadiene;
h) alkylation of n-butene present in the hydrocarbon mixture with isobutane likewise present;
i) oxidation of hydrocarbons having four carbon atoms present in the hydrocarbon mixture for preparation of maleic anhydride.

It will be appreciated that not all the workup steps a) to i) enumerated need be conducted; it is also possible to conduct only individual workup steps. The sequence enumerated is not binding either.

Furthermore, individual workup steps among those enumerated may also be arranged upstream of the inventive purification, provided that they are not sensitive to the catalyst poisons. At least a nickel-catalysed oligomerization should be protected by the purification process according to the invention, since organic sulphur compounds, even in very small concentrations, poison nickel catalysts.

If the hydrocarbon mixture used is also contaminated with water, it is advisable to free the water-contaminated hydrocarbon mixture of water before contact with the sorbent, i.e. to dry it. The motivation for removing the water is as follows: Since homogeneously dissolved water in the mixture somewhat attenuates the action of the sorbent, the stream is preferably dried before contact with the sorbent, for example by means of an azeotropic distillation (drying distillation). The drying is effected prior to the addition of the hydrogen if at all possible.

EXAMPLES

First Experiment

Removal of Ethanethiol According to the Invention

The sorbent used is a solid purchased from Clariant AG, which is usable as methanol catalyst. The sorbent contains about 42% by weight of CuO, about 44% by weight of ZnO, about 12.5% by weight of $Al_2O_3$ and about 2% by weight of graphite, and is in the form of tablets (5×3 mm). The specific copper oxide surface area, measured by means of nitrogen sorption, is 100 $m^2$ per g of copper oxide content.

27 g of sorbent are introduced into a reaction tube having diameter 1 cm. The bulk density is about 1.2 $kg/dm^3$. A sampling valve is mounted in the feed and in the outlet of the tube. The sorbent is brought to a temperature of 80° C. by heating the tube wall, and a liquid mixture containing about 37% by weight of 1-butene, about 24% by weight of trans-2-butene, about 14% by weight of cis-2-butene and about 24% by weight of n-butane and 252 ppm by weight of homogeneously dissolved $H_2$ is allowed to flow through them at a pressure of 21 bar. As contaminant, the material contains an average of 21.8 mg/kg of sulphur, predominantly in the form of ethanethiol. The load on the sorbent is 357 g/h, and so the sulphur input is about 7.8 mg/h. As shown by the analyses, the sulphur is removed virtually quantitatively from the mixture. From an operating time of 281 hours onward, the sulphur content at the outlet rises rapidly. This sharp breakthrough corresponds to an arrested amount of sulphur of about 2.1 g or a sulphur sorption by the sorbent of about 7.8% by weight. The output values of the individual C4 components remained virtually unchanged compared to the corresponding feed values over the entire experimental period. After the end of this experiment, the bed comprising the sorbent is purged with nitrogen. The sorbent can be removed intact and with sufficient stability. The results of the experiment are recorded in Table 1.

TABLE 1

Results from experiment 1

| Mean S content [% by wt.] in feed | Mean S content [% by wt.] in output up to 281 h | Mean decrease in S [% by wt.] in output compared to feed up to 281 h | Mean 1-butene conversion [%] up to 281 h |
| --- | --- | --- | --- |
| 0.00218 | 0.00006 | 97 | 2.3 |

Second Experiment

Removal of Methanethiol According to the Invention

The sorbent used and the experimental setup correspond to the first experiment. Analogously to experiment 1, an average of 20.6 mg/kg of sulphur is supplied as impurity, predominantly in the form of methanethiol. The content of homogeneously dissolved $H_2$ is 170 ppm by weight. The load on the sorbent, charged in an amount of 28 g, is 350 g/h, i.e. the sulphur input is about 7.2 mg/h. The contact temperature was set to 80° C. As shown by the analyses in the sorbent, the sulphur is removed virtually quantitatively from the mixture. From an operating time of about 295 hours onward, the sulphur content at the outlet rises. This sharp breakthrough corresponds to an arrested amount of sulphur of about 2.1 g or a sulphur sorption by the sorbent of about 7.6% by weight. The output values of the individual C4 components remained virtually unchanged compared to the corresponding feed values over the entire experimental period. After the end of this experiment, the beds are purged with nitrogen. The sorbent can be removed intact and with sufficient stability. The experimental results are shown in Table 2.

TABLE 2

Results from experiment 2

| Mean S content [% by wt.] in feed | Mean S content [% by wt.] in output up to 295 h | Mean decrease in S [% by wt.] in output compared to feed up to 295 h | Mean 1-butene conversion [%] up to 295 h |
| --- | --- | --- | --- |
| 0.00206 | 0.00007 | 97 | 1.9 |

Third Experiment

Removal of Diethyl Disulphide According to the Invention

The sorbent used and the experimental setup correspond to the first and second experiments. Analogously to experiment 1, about 1 mg/kg of sulphur is supplied as impurity, in the form of diethyl disulphide. The supplied concentration of homogeneously dissolved $H_2$ is 170 ppm by weight. The load on the bed, containing 27 g of the sorbent, is 350 g/h, and so the sulphur input is about 0.35 mg/h. The operating temperature is 80° C. As shown by the analyses, the sulphur is removed quantitatively from the mixture. Up to an operating time of 2865 hours, no sulphur components at all could be detected in the output. Up to that point, about 0.91 g of sulphur had been arrested. This corresponds to a sulphur sorption by the sorbent of about 3.3% by weight by this time. The output values of the individual C4 components remained virtually unchanged compared to the corresponding feed values over the entire experimental period. The experimental results are shown in Table 3.

TABLE 3

Results from experiment 3

| Mean S content [% by wt.] in feed | Mean S content [% by wt.] in output up to 2865 h | Mean decrease in S [% by wt.] in output compared to feed up to 2865 h | Mean 1-butene conversion [%] up to 2865 h |
|---|---|---|---|
| 0.000082 | 0.000000 | 100 | 1.6 |

Fourth Experiment

Removal of Ethanethiol (Noninventive)

The sorbent used and the experimental setup correspond to the first experiment. However, the experiment is conducted without metered addition of hydrogen.

As a contaminant, the material contains an average of 5.4 mg/kg of sulphur, predominantly in the form of ethanethiol. The load on the bed, containing 120 g of the adsorbent, is 600 g/h, and so the sulphur input is about 3.2 mg/h.

As shown by the analyses, the sulphur is at first removed virtually quantitatively from the mixture. From an operating time of 480 hours onward, the sulphur content at the outlet rises rapidly. This sharp breakthrough corresponds to an arrested amount of sulphur of about 1.7 g or a sulphur sorption by the sorbent of about 1.4% by weight.

The discharge values of the individual $C_4$ components remained unchanged compared to the corresponding feed values over the entire experimental period.

After the end of this experiment, the bed is purged with nitrogen. The sorbent can be removed intact and with sufficient stability.

The results of the experiment are recorded in Table 4.

TABLE 4

Results from experiment 4

| Mean S content [% by wt.] in feed | Mean S content [% by wt.] in output up to 480 h | Mean decrease in S [% by wt.] in output compared to feed up to 480 h | Mean 1-butene conversion [%] up to 480 h |
|---|---|---|---|
| 0.00054 | 0.00003 | 94 | 0.3 |

Conclusions from the Experiments

The experiments demonstrate that the process conducted in accordance with the invention, by virtue of the combination of a suitable sorbent with metered addition of hydrogen, has the following properties:
  sulphur from various sulphur compounds is virtually fully bound;
  the sorbent does not require any activation in the hydrogen stream;
  the sorbent does not require any periodic purifying and desorption streams, since it is an irreversible sorbent;
  the sorbent can be accommodated in a simple vessel through which the mixture simply flows, preferably at slightly elevated temperature, as is typically often necessary in any case for the feeding of downstream reactors;
  in spite of metered addition of hydrogen, the process causes virtually no side reactions of the olefins, such as oligomerization, isomerization and hydrogenation, and hence no significant losses of the constituents of value of the mixture to be purified either;
  the metered addition of hydrogen increases the capacity and hence the service life of the sorbent compared to the prior art known to date;
  the process does not release any substances whatsoever in concentrations that have any influence at all on the downstream processing stages;
  in view of the long lifetime at typical sulphur concentrations below 5 ppm by weight, accounted for by the capacity of the sorbent of at least 3% by weight of sulphur, the process is very inexpensive to operate, even though the sorbent cannot be regenerated directly, and can instead only be sent to a raw material utilization after the capacity has been exhausted; this seems attractive because of the high copper content;
  the sorbent can be handled and disposed of without any problem, since it is neither classified as carcinogenic nor exhibits pyrophoric properties.

What is claimed is:

1. A process for purifying hydrocarbon mixtures, in which a contaminated hydrocarbon mixture comprising olefins is at least partly freed of sulphur-containing contaminants by contacting the contaminated hydrocarbon mixture with a solid sorbent in the presence of hydrogen, wherein the contaminated hydrocarbon mixture, immediately prior to the contacting with the solid sorbent, contains hydrogen in a concentration, based on the total mass of the contaminated hydrocarbon mixture, between 1 ppm by weight and 10 000 ppm by weight, wherein the contaminated hydrocarbon mixture is exclusively in the liquid state during the contacting with the solid sorbent wherein the contaminated hydrocarbon mixture comprises 1-butene and the contacting with the solid sorbent converts less than 5% by weight of the 1-butene in the contaminated hydrocarbon mixture, wherein the solid sorbent has the following composition that adds up to 100% by weight:
  copper oxide: 10% by weight to 60% by weight calculated as CuO;
  zinc oxide: 10% by weight to 60% by weight calculated as ZnO;
  aluminium oxide: 10% by weight to 30% by weight calculated as $Al_2O_3$; and
  other substances: 0% by weight to 5% by weight,
  wherein the solid sorbent has a copper oxide surface area of at least 50 $m^2/g$,
  and wherein the contaminated hydrocarbon mixture fulfills one of the following specifications A, B, C and D, each of which adds up to 100% by weight, the stated proportions by weight each being based on the total weight of the contaminated hydrocarbon mixture:
  Specification A:
    isobutane 15% to 45% by weight;
    n-butane 5% to 18% by weight;
    1-butene 5% to 20% by weight;
    isobutene 12% to 25% by weight;
    2-butenes 9% to 40% by weight;
    1,3-butadiene 0% to 3% by weight;
    water 0% to 1% by weight;
    sulphur-containing impurities less than 0.5% by weight; and
    hydrogen less than 1 ppm by weight;
  Specification B:
    isobutane 0.5% to 15% by weight;
    n-butane 0.5% to 20% by weight;
    1-butene 9% to 25% by weight;

isobutene 10% to 35% by weight;
2-butenes 3% to 15% by weight;
1,3-butadiene 25% to 70% by weight;
water 0% to 1% by weight;
sulphur-containing impurities less than 0.5% by weight; and
hydrogen less than 1 ppm by weight;
Specification C:
isobutane 0.5% to 18% by weight;
n-butane 0.5% to 25% by weight;
1-butene 9% to 40% by weight;
isobutene 10% to 55% by weight;
2-butenes 3% to 25% by weight;
1,3-butadiene 0% to 5% by weight;
water 0% to 1% by weight;
sulphur-containing impurities less than 0.5% by weight; and
hydrogen less than 1 ppm by weight; and
Specification D:
isobutane 0% to 20% by weight;
n-butane 10% to 35% by weight;
1-butene 0.2% to 45% by weight;
2-butenes 35% to 85% by weight;
water 0% to 1% by weight;
sulphur-containing impurities less than 0.5% by weight; and
hydrogen less than 1 ppm by weight.

2. The process according to claim 1, wherein the hydrogen is fully dissolved in the contaminated hydrocarbon mixture in the liquid state.

3. The process according to claim 1, wherein the concentration of hydrogen is established by adding hydrogen to the contaminated hydrocarbon mixture immediately prior to the contacting with the solid sorbent, wherein the contaminated hydrocarbon mixture prior to addition of the hydrogen contains less than 1 ppm by weight of hydrogen.

4. The process according to claim 1, wherein the solid sorbent has the following composition that adds up to 100% by weight:
copper oxide: 30% by weight to 45% by weight calculated as CuO;
zinc oxide: 30% by weight to 50% by weight calculated as ZnO;
aluminum oxide: 10% by weight to 15% by weight calculated as $Al_2O_3$;
further metal oxides: 0% by weight to 2% by weight;
graphite: 0% by weight to 3% by weight; and
other substances: 0% by weight to 1% by weight.

5. The process according to claim 1, wherein the contacting with the solid sorbent is conducted under the following conditions:
a temperature range between 10° C. and 150° C.;
a pressure range between 0.5 and 3.5 MPa; and
a weight hourly space velocity range between 0.5 $h^{-1}$ and 20 $h^{-1}$.

6. The process according to claim 1, wherein the contaminated hydrocarbon mixture contains, as sulphur-containing contaminant, at least one compound from one of the following substance classes:
a) thiols having the general formula R—SH where R is an alkyl, aryl, cycloalkyl or alkenyl radical;
b) disulphides having the general formula R—S—S—R' where R and R' are identical or different alkyl, aryl, cycloalkyl or alkenyl radicals;
c) sulphides having the general formula R—S—R' where R and R' are identical or different alkyl, aryl, cycloalkyl or alkenyl radicals; and
d) substituted or unsubstituted sulphur-containing heterocycles.

7. The process according to claim 6, wherein the contaminated hydrocarbon mixture contains less than 0.2% by weight of the sulphur-containing contaminants, calculated as sulphur based on the total weight of the contaminated hydrocarbon mixture.

8. The process according to claim 7, wherein the contaminated hydrocarbon mixture is freed by the contacting with the solid sorbent of at least 90% by weight of the sulphur-containing contaminants present in the contaminated hydrocarbon mixture.

9. The process according to claim 7, wherein the contaminated hydrocarbon mixture is obtained from a pre-purification stage which pre-purifies a more highly contaminated raw material mixture to obtain the contaminated hydrocarbon mixture.

10. The process according to claim 9, wherein the solid sorbent is used irreversibly.

11. The process according to claim 1, wherein a hydrocarbon mixture which has been at least partly freed of contaminants by the process according to claim 1 is subjected to at least one of the workup steps enumerated below:
a) extraction of 1,3-butadiene present in the hydrocarbon mixture;
b) selective hydrogenation of diolefins and/or acetylenes present in the hydrocarbon mixture to olefins;
c) oligomerization of olefins present in the hydrocarbon mixture to corresponding oligomers;
d) distillative removal of 1-butene and/or isobutane present in the hydrocarbon mixture;
e) removal of isobutene present in the hydrocarbon mixture by conversion of the isobutene with water to tert-butanol and/or with methanol to methyl tert-butyl ether;
f) dehydrogenation of butanes present in the hydrocarbon mixture to butenes;
g) oxidative dehydrogenation of butenes present in the hydrocarbon mixture to butadiene;
h) alkylation of n-butene present in the hydrocarbon mixture with isobutane present therein; and
i) oxidation of hydrocarbons having four carbon atoms present in the hydrocarbon mixture for preparation of maleic anhydride.

* * * * *